United States Patent
Steengaard et al.

[11] Patent Number: 5,951,530
[45] Date of Patent: Sep. 14, 1999

[54] INJECTION NEEDLE

[75] Inventors: Kim Steengaard, Birkerød; Steffen Lav, Brønshøj, both of Denmark

[73] Assignee: Novo Nordisk A/S, Bagsvaerd, Denmark

[21] Appl. No.: 08/840,060

[22] Filed: Apr. 24, 1997

[30] Foreign Application Priority Data

Apr. 24, 1996 [DK] Denmark .................. 0491/96

[51] Int. Cl.[6] .................................................. A61M 5/158
[52] U.S. Cl. ........................................... 604/272; 604/413
[58] Field of Search .............................. 606/181; 604/272, 604/411, 412, 413, 414

[56] References Cited

FOREIGN PATENT DOCUMENTS 0 279 583  8/1988  European Pat. Off. .
WO 90/07348  7/1990  WIPO .
WO 93/00948  1/1993  WIPO .

*Primary Examiner*—Michael H. Thaler
*Attorney, Agent, or Firm*—Steve T. Zelson, Esq.

[57] ABSTRACT

The present invention relates to a needle mounted in a needle hub fitting onto an injection device from which preset doses of a medicine from a cartridge accommodated in the device is administered through the needle comprises a back needle penetrating a closure membrane of the cartridge and a free injection part shorter than 9 mm, the outer diameter of the needle and the diameter of its bore complying with one of the conditions: a) the outer diameter is smaller than 0.320 mm and the diameter of the bore is larger than 0.165 mm, or b) the outer diameter is smaller than 0.298 mm and the diameter of the bore is larger than 0.133 mm.

8 Claims, 1 Drawing Sheet

INJECTION NEEDLE

CROSS-REFERENCE TO RELATED APPLICATIONS

This application claims priority under 35 U.S.C. 119 of Danish application 0491/96 filed Apr. 24, 1996, the contents of which are fully incorporated herein by reference.

BACKGROUND OF THE INVENTION

1. Field of the Invention

The present invention relates to injection needles especially needles mounted in a needle hub fitting onto an injection device of the kind from which preset doses of a medicine from a cartridge accommodated in the device may be administered through the needle mounted on the device and exposing a back needle penetrating a closure membrane of the cartridge and a free injection part.

2. Description of Related Art

Such an injection device, by which doses may be set individually and on which a needle may be mounted and changed after having been used for injection of a medicine from a cartridge in the device, is a common tool for people who have to inject themselves one or more times a day as it is the case by people who are treated with growth hormone or by diabetics who have to inject themselves frequently to keep their blood sugar on an acceptable level.

To reduce the malaise by frequent pricking of the skin the trend has lead towards use of still thinner needles as it have shown to cause less pain to be pricked with a fine needle than with a coarse one. With finer needles other problems occur one of them being that e.g. some kinds of insulin has coarse crystals which tends to clog at the inlet to the needle and in this way be sieved from the liquid in which the crystals are suspended. This way the concentration of the insulin injected may differ from what the user think it is which may cause injection of a wrong dose.

These problems has according to WO 93/00948 been overcome by using needles mounted in special needle hubs which fit only on devices about which it is known that they will only contain insulin which may flow freely through a thin needle defined as a G30 needle. This is obtained by making devices for which it is guaranteed that they will only contain insulin having a grain size less than 15 $\mu$m and provide the devices with needle receiving pieces onto which the hubs with the fine needles fits. It may be noticed that thicker needles of course may be provided with a corresponding hub as the insulin in the device of course without problems may pass a thicker needle having a larger bore.

Although G30 needles cause less pain and allow even crystalline insulin to pass provided the crystals have no dimensions larger than 15 $\mu$m, the use of these needles is not without problems even by injection of solutions. One of the problems is that a relatively high pressure has to be established in the cartridge from which the medicine shall be pressed out which again means that an excessive force has to be exerted on a manually operated injection button. This may make it difficult for users with weak fingers to perform the injection sufficiently rapidly. With the high pressure in the cartridge, which is mainly of the kind wherein a piston closes one end of an cylinder ampoule whereas the other is closed by a rubber membrane which may be penetrated by a back needle of a double pointed needle to provide communication from the content of the ampoule through the hollow needle to the injection point of this needle, elasticity of the cartridge parts, especially the rubber membrane and the piston, may cause dripping from the needle when this needle is drawn out from the tissue into which it has been inserted during the injection. This means that not the whole set dose is actually injected.

It is the object of the invention to provide a thin needle by which the advantages of the G30 needle are enhanced and/or the drawbacks of this needle are overcome.

SUMMARY OF THE INVENTION

The present invention relates to injection needles especially needles mounted in a needle hub fitting onto an injection device of the kind from which preset doses of a medicine from a cartridge accommodated in the device may be administered through the needle mounted on the device and exposing a back needle penetrating a closure membrane of the cartridge and a free injection part.

BRIEF DESCRIPTION OF THE DRAWINGS

In the following the invention is explained in more details with reference to the drawing in which.

DETAILED DESCRIPTION OF THE INVENTION

Figure 1:
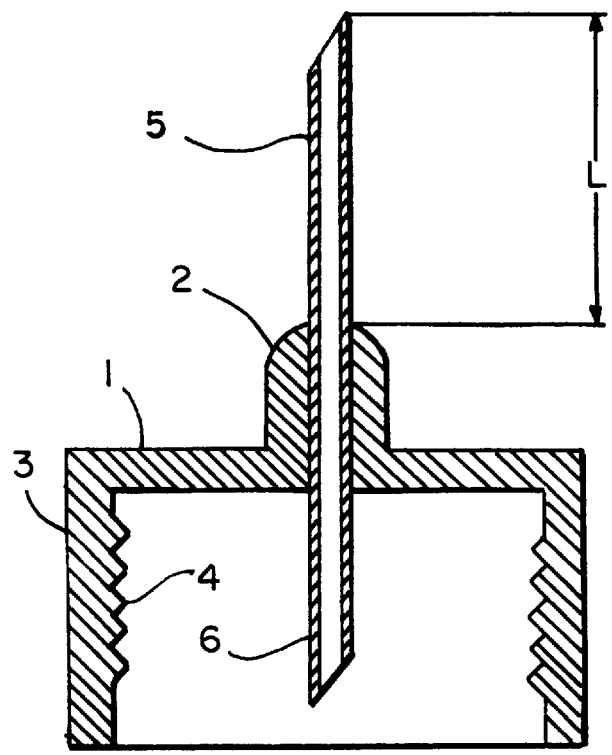
FIG. 1 shows schematically a sectional view of a needle hub with a needle according to the invention.

The needles of the present invention are characterized in that the length of the injection part is shorter than 9 mm and that the outer diameter and bore of the needle complies with one of the conditions:

a) the outer diameter is smaller than 0.320 mm and the diameter of the bore is larger than 0.165 mm, or b) the outer diameter is smaller than 0.298 mm and the diameter of the bore is larger than 0.133 mm.

As the standard ISO 7864 describes tolerances for injection needles defining that the length of a needle may be one millimeter longer or two millimeter shorter than the nominal length of the needle, and as the standard ISO 9626 specifies that for an ordinary G30 the outer diameter of the needle must be found within the range between 0.320 mm and 0.298 mm, and the diameter of the bore must be found within the range between 0.133 mm and 0.165 mm, the characterizing clause may alternatively be worded as follows:

that the length of the injection part is nominally 8 mm or less, and that one of the following two conditions is complied with:
a) the outer diameter corresponds to the outer diameter of a G30 needle and the bore diameter is larger than the bore diameter of an ordinary G30 needle, or
b) the outer diameter is smaller than the outer diameter of a G30 needle and the diameter of the bore is larger than the minimum diameter of the bore in an ordinary G30 needle.

From WO 93/00948 it is known to use G30 needles for injection of insulin from a pen accommodating a cartridge with an insulin having a maximal crystal size of 15 $\mu$m. This will guarantee that the insulin stored in such injection devices will be able to ran freely through needles having a bore with diameter larger than 0.133 mm which is the smallest bore occurring in a normal G30 needle. Other kinds of medicine not containing crystals at all will of course also be able to pass such a normal G30 needle.

The use of the smaller wall thickness by needles having outer diameters smaller than 0.320 mm will allow a larger bore in a G30 needle with a resulting better flow through the needle. Alternatively, if a bore diameter of 0.133 mm is accepted the use of thin walls may allow a needle which is still thinner than a G30 needle but which nevertheless guarantees free flow of even a crystalline insulin in the device.

Thin walled G30 needles are known, but as it has been the view that thin needles with thin walls should be handled by professionals due to the risk of breaking the needle, thin walled needles have not previously been manufactured for use with injection devices designed for self administration of medicine, e.g. insulin. However, as described in WO 93/00948, needles as thin as a normal G30 have shown to be safe for use by self injection and as the bending strength of the needle tube is only reduced 6% when the wall thickness is reduced 50% a short thin walled needle will be safe too even in the hand of non professionals.

According to the invention the injection part of the needle is shorter than 9 mm and may appropriately be 4–8 mm. With a shorter needle the risk for breaking will be reduced, and further, short needles are to be preferred for subcutaneous injections as the use of short needles reduces the risk of inserting the needle deeper than subcutis. As further the needle is used with an injection device of the kind from which preset doses of a medicine are administrated from a cartridge, the needle part which has to penetrate the closure membrane is the short back needle which may be passed through the membrane without any risk for unallowable bending.

In FIG. 1 a needle is mounted in a needle hub comprising a circular disc shaped element 1 which has along its periphery a circumferential depending sleeve which is on its inner wall provided with a thread 4 by which the needle hub may be screwed onto a needle receiving part of a syringe which needle receiving part is provided with an outer thread. At its center the element 1 is provided with a protrusion 2 projecting from the disc in the opposite direction of the sleeve. Centrally through the protrusion 2 and the disc element 1 a double pointed needle is mounted so that one pointed end part 5 forming an injection part for piercing the skin of a user protrudes from the protrusion 2 and a so-called back needle 6 protrudes from the opposite side of the circular disc so that it is concentrically surrounded by the sleeve 3. The back needle 6 is shorter than the sleeve 3 so that this sleeve to some extent protects the pointed end of the back needle. The injection part 5 of the needle has a length L which is smaller than 9 mm which is according to ISO 7864:1993E the maximal length accepted for a needle denounced as an 8 mm needle. By limiting and reducing this length the bending moment exerted on the injection part 5 of the needle during insertion of this part through the skin is reduced. The back needle 6 which has to penetrate a closing membrane of an ampoule when the needle is mounted on a syringe is still shorter. This is advantageous as such a membrane is more difficult to penetrate than is the skin. The limited lengths of the unsupported needle makes a reduction of the wall thickness and the resulting reduction of the bending strength acceptable.

Figure 2:
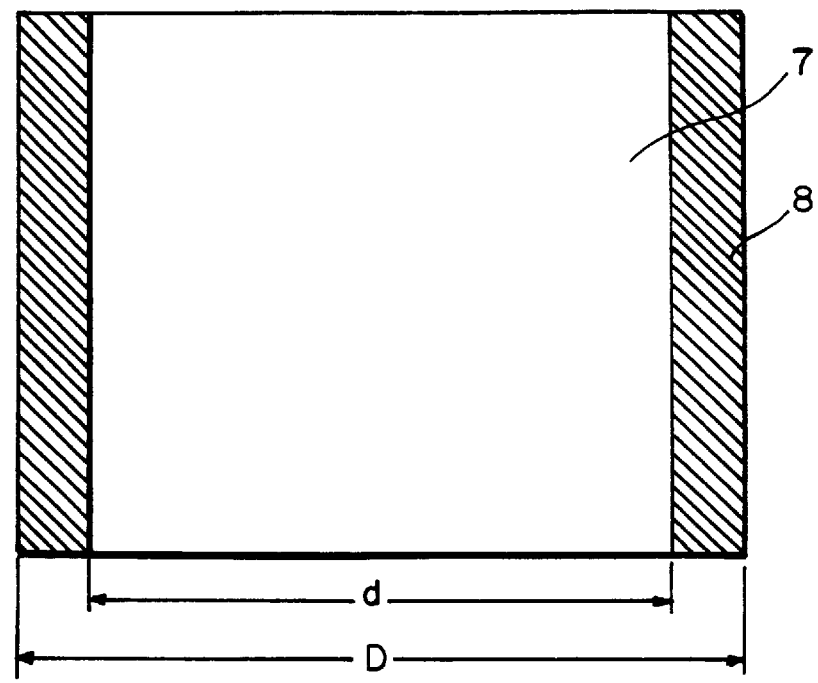
FIG. 2 shows a sectional view of a section of the needle tube.

FIG. 2 shows schematically a sectional view of a section of a needle tube presenting a wall 8 and a bore 7. The needle is characterized by its outer diameter D and the diameter d of the bore. A reduction of the wall thickness may be used for obtaining a larger bore diameter d in a needle as thin as G30 according to ISO 9626 or for obtaining a needle which has a bore diameter d at least corresponding to the minimum diameter of a G30 needle and an outer diameter D smaller than the minimum diameter of a G30 needle. This may be expressed by the conditions:

$d \geq 0.165$ mm and $D \leq 0.320$ or
$d \geq 0.133$ mm and $D \leq 0.298$ mm taken with the following condition which must always be complied with: $d + 2 \times$(wall thickness)$= D$.

The smallest wall thickness which may be accepted is defined by the demands set on the bending strength of the needle.

We claim:

1. A needle assembly comprising an injection needle mounted in a needle hub and having first and second needle portions extending therefrom, wherein said needle hub is designed to fit onto an injection device containing a cartridge sealed by a membrane such that said first needle portion penetrates such membrane, and wherein said second needle portion may be inserted into a patient such that preset doses of a medicine from such cartridge may be administered, wherein said second needle portion projects from said hub by a distance which is less than 9 mm, and wherein said needle has an outer diameter and a bore diameter which comply with one of the following conditions:

a) the outer diameter is smaller than 0.320 mm and the diameter of the bore is larger than 0.165 mm, or b) the outer diameter is smaller than 0.298 mm and the diameter of the bore is larger than 0.133 mm.

2. A needle assembly according to claim 1, wherein the needle hub is designed to fit onto an injection system for insulin.

3. A needle assembly according to claim 2, wherein said hub is designed to fit on a mounting for an injection system which accommodates only cartridges with insulin types which are solutions or suspensions with particles having a diameter not exceeding 15 μm.

4. A needle assembly according to claim 1, wherein the needle hub is designed to fit onto an injection system for insulin analogues.

5. A needle assembly according to claim 1, wherein the needle hub is designed to fit onto an injection system for growth hormones.

6. A needle assembly according to claim 1, wherein said second needle portion has a length which is at least 4 mm and which is less than 8 mm.

7. A needle assembly according to claim 6, wherein the outer diameter is within the ISO-specified range for a G30 needle, and the bore diameter is larger than the ISO-specified bore diameter of a G30 needle.

8. A needle assembly according to claim 6, wherein the outer diameter is smaller than the ISO-specified range for a G30 needle, and the bore diameter is within the ISO-specified range for a G30 needle.

* * * * *